United States Patent
Uhlemann et al.

(10) Patent No.: US 10,092,775 B2
(45) Date of Patent: Oct. 9, 2018

(54) MEDICAL INSTRUMENT FOR EXTERNAL BEAM RADIOTHERAPY AND BRACHYTHERAPY

(71) Applicant: KONINKLIJKE PHILIPS N.V., Eindhoven (NL)

(72) Inventors: Falk Uhlemann, Hamburg (DE); Johannes Overweg, Uelzen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 293 days.

(21) Appl. No.: 15/024,402

(22) PCT Filed: Sep. 25, 2014

(86) PCT No.: PCT/EP2014/070428
§ 371 (c)(1),
(2) Date: Mar. 24, 2016

(87) PCT Pub. No.: WO2015/044239
PCT Pub. Date: Apr. 2, 2015

(65) Prior Publication Data
US 2016/0213949 A1    Jul. 28, 2016

(30) Foreign Application Priority Data

Sep. 30, 2013    (EP) .................................... 13186645

(51) Int. Cl.
*A61N 5/10*    (2006.01)
*A61M 36/00*    (2006.01)
*A61B 90/00*    (2016.01)

(52) U.S. Cl.
CPC .......... *A61N 5/1039* (2013.01); *A61N 5/1001* (2013.01); *A61N 5/1071* (2013.01);
(Continued)

(58) Field of Classification Search
CPC ... A61N 5/103–5/1047; A61N 5/1077–5/1084
See application file for complete search history.

(56) References Cited

U.S. PATENT DOCUMENTS 5,882,291 A * 3/1999 Bradshaw ............ A61N 5/1002
600/3
8,112,143 B2  2/2012 Van Vaals
(Continued)

FOREIGN PATENT DOCUMENTS

EP    1440708 A1 * 7/2004   ........... A61N 5/1007
EP    2535086       12/2012
(Continued)

OTHER PUBLICATIONS

Hurwitz Mark D et al. Combination External Beam Radtiation and Brachytherapy Booth With Androgen Deprivation for Treatment of Intermediate-Risk Prostate Cancer. Cancer 2011; 117:5579-88.*
(Continued)

*Primary Examiner* — Catherine B Kuhlman

(57) ABSTRACT

The invention provides for a medical instrument (400, 500, 600, 700) comprising a magnetic resonance imaging system (404) and an external beam radiotherapy system (402) for irradiating a target zone (438) of a subject with a beam (442) of ionizing radiation within the imaging zone. The medical instrument further comprises a processor (448) for controlling the medical instrument. Execution of instructions cause the processor to: acquire (100, 200) first magnetic resonance data (458); reconstruct (102, 202) a first magnetic resonance image (460) from the first magnetic resonance data; receive (104, 204) planning data (462), wherein the planning data specifies a spatially dependent radiation dose for the target zone; register (106, 206) the planning data to the first magnetic resonance image; and calculate (108, 208) an external beam dosage plan (468) and a brachytherapy dos-
(Continued)

age plan (468) using the spatially dependent radiation dose and the first magnetic resonance image.

14 Claims, 9 Drawing Sheets

(52) U.S. Cl.
CPC ...... *A61N 5/1077* (2013.01); *A61B 2090/374* (2016.02); *A61B 2090/3954* (2016.02)

(56) References Cited

U.S. PATENT DOCUMENTS

| | | | |
|---|---|---|---|
| 8,190,233 B2 | 5/2012 | Dempsey | |
| 9,101,395 B2 | 8/2015 | Gutierrez | |
| 2002/0091315 A1 | 7/2002 | Spetz | |
| 2005/0027196 A1* | 2/2005 | Fitzgerald | A61N 5/103 600/436 |
| 2011/0160566 A1 | 6/2011 | Petropoulos | |
| 2012/0184841 A1* | 7/2012 | Nielsen | A61N 5/1031 600/411 |

FOREIGN PATENT DOCUMENTS

| | | | |
|---|---|---|---|
| WO | 2012063162 | 5/2012 | |
| WO | 2012/080949 | 6/2012 | |
| WO | 2012/137148 | 10/2012 | |
| WO | 2013/057609 | 4/2013 | |
| WO | WO 2013057609 A1 * | 4/2013 | ........... A61N 5/1027 |

OTHER PUBLICATIONS

Williamson J.F. (2006) Integration of IMRT and Brachytherapy. In: Bortfeld T., Schmidt-Ullrich R., De Neve W., Wazer D.E. (eds) Image-Guided IMRT. Springer, Berlin, Heidelberg.*

Georg, et al., "Correlation of dose-volume parameters, endoscopic and clinical rectal side effects in cervix cancer patients treated with definitive radiotherapy including MRI-based brachytherapy", Radiotherapy and Oncology, 2009, vol. 91, No. 2, p. 173-180.

Sakamoto, et al., "Clinical Outcome in Prostate Cancer Patients Undergoing High-Dose-Rate Brachytherapy With External Beam Radiotherapy in Our Institute" 2011 Japanese Urological Association, Abstract.

* cited by examiner

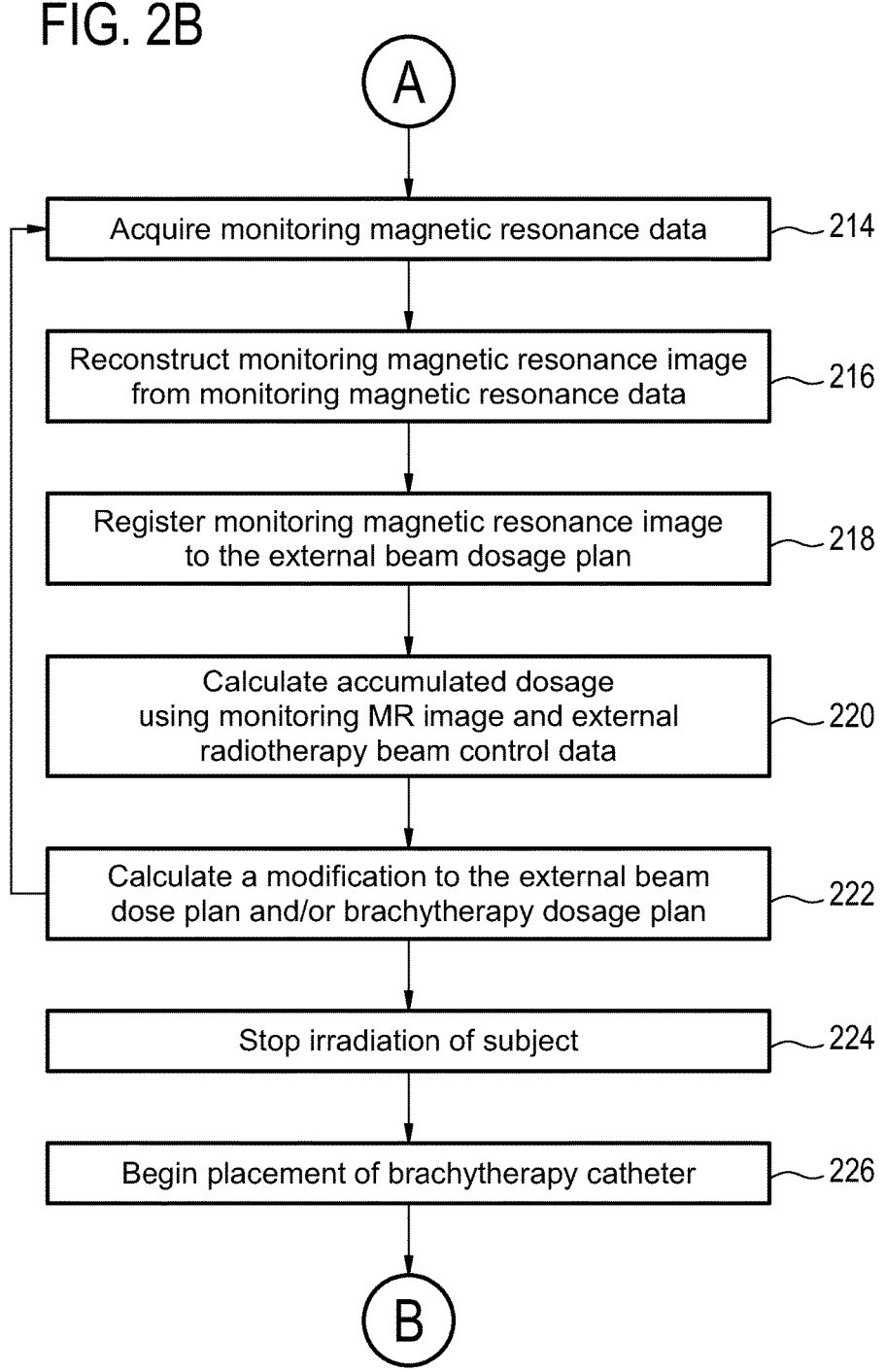

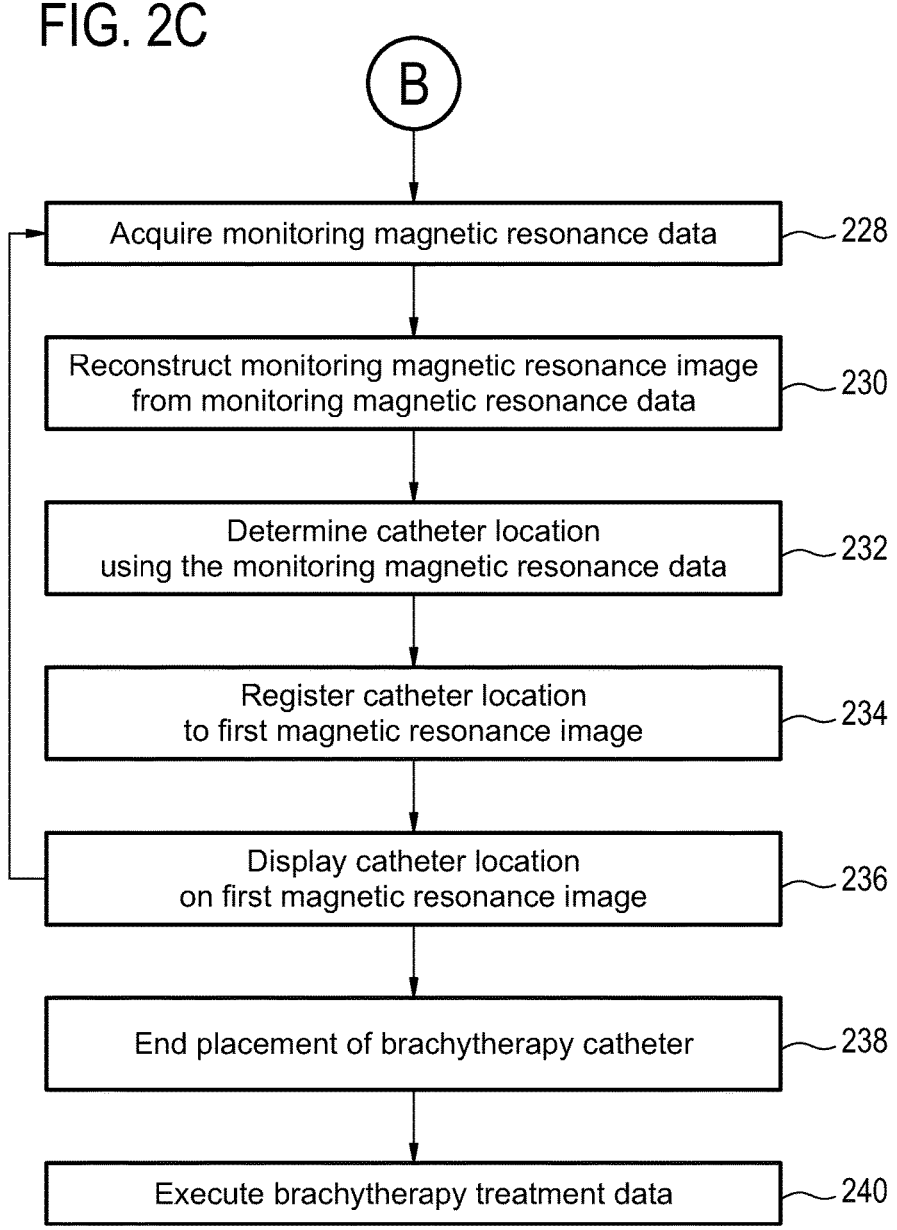

MEDICAL INSTRUMENT FOR EXTERNAL BEAM RADIOTHERAPY AND BRACHYTHERAPY

CROSS REFERENCE TO RELATED APPLICATIONS

This application is the U.S. National Phase application under 35 U.S.C. § 371 of International Application No. PCT/EP2014/070428, filed Sep. 25, 2014, published as WO 2015/044239 on Apr. 2, 2015, which claims the benefit of European Patent Application Number 13186645.1 filed Sep. 30, 2013. These applications are hereby incorporated by reference herein.

TECHNICAL FIELD

The invention relates to the planning of external beam radiotherapy and brachytherapy.

BACKGROUND OF THE INVENTION

Integration of MR and Linear Accelerators (LINAC) opens new horizons in Radiotherapy by improved lesion targeting, especially for moving organs. In a practical implementation proposal, the LINAC rotates around the subject to hit the gross target volume (GTV) and clinical target volume (CTV) from multiple angles while minimizing the radiation exposure for surrounding tissues.

The combination of magnetic resonance apparatuses and LINAC radiotherapy sources is known. Typically a LINAC source is placed on a rotating gantry about the magnet and the magnet designed such that the LINAC rotates in a zero-field region of the magnet. Another particular feature of the concept is the use of a split gradient coil which prevents attenuation of the LINAC beam.

In brachytherapy, a catheter is inserted into a subject. Then a radioactive source is controllably inserted into the catheter to irradiate the subject. In brachytherapy systems (e.g. for high dose rate brachytherapy) the radioactive source can be withdrawn from the catheter after a predetermined amount of time.

United Stated Patent application US 2011/0160566 discloses the guiding of electron beam or X-ray beam therapy and brachytherapy using a magnetic resonance imaging system by registering ultrasound images to a previously acquired magnetic resonance image.

SUMMARY OF THE INVENTION

The invention provides for a medical instrument, a computer program product, and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical instrument comprising a magnetic resonance imaging system for acquiring magnetic resonance data from a subject within an imaging zone. The medical instrument further comprises an external beam radiotherapy system for irradiating a target zone with a beam of ionizing radiation within the imaging zone. The external beam radiotherapy system may be any system which is operable for generating a beam of ionizing radiation for irradiating the target zone. For example the external beam radiotherapy system may be a so called linear accelerator or LINAC. The medical instrument further comprises a memory for storing machine-executable instructions. The medical instrument further comprises a processor for controlling the medical instrument.

Execution of the machine-executable instructions causes the processor to acquire first magnetic resonance data from the subject using the magnetic resonance imaging system. Execution of the instructions further cause the processor to reconstruct a first magnetic resonance image from the first magnetic resonance data. The first magnetic resonance image is a label for a magnetic resonance image or data which is in a form which can be rendered as an image. The first magnetic resonance image may for instance be a single slice or it may include multiple magnetic resonance imaging slices. Execution of the instructions further causes the processor to receive planning data. The planning data specifies a spatially dependent radiation dose for the target zone. The planning data may for instance be data which was generated previously and specifies a region of the subject to be irradiated. The planning data may also comprise other information or data. For instance, the planning data may contain data descriptive of the position of the spatially dependent radiation dose relative to anatomical landmarks which can be identified in a magnetic resonance imaging of the subject.

Receiving the planning data may also be receiving the planning data from for instance a graphical user interface. For instance the first magnetic resonance image may be displayed on a display and the graphical user interface may be used to enter the planning data into a computer or user interface. Execution of the instructions further causes the processor to register the planning data to the first magnetic resonance image. Registering the planning data to the first magnetic resonance image enables the planning data to be applied to the subjects anatomy as it is positioned the medical apparatus.

If the planning data was entered with reference to the first magnetic resonance image on a user interface then the registration would be automatic by nature of how the data were entered. In other embodiments there may need to be some sort of pattern recognition or alignment between coordinate systems of the planning data and the first magnetic resonance image. This could be achieved for instance by identifying anatomical landmarks in both the planning data and the first magnetic resonance image and aligning them.

Execution of the instructions further cause the processor to calculate an external beam dosage plan and a brachytherapy dosage plan using the spatially dependent radiation dose and the first magnetic resonance image That is, the calculation involves a decomposition of the spatially dependent radiation dose registered to the first magnetic resonance image into contributions due the external beam dosage plan and the brachytherapy dosage plan, respectively. Thus, the brachytherapy dosage plan and eh external dosage plan are generated that when put into operation form the spatially radiation dose from the planning data and corrected for changed positions by way of the registration to the first magnetic resonance image. The external beam dosage plan is a plan or commands for specifically irradiating the target zone using the external beam radiotherapy system. This can be done using the first magnetic resonance or other pretreatment data so the subject may be irradiated without the subject moving and having a change in its internal coordinates system. The brachytherapy dosage plan is a plan for irradiating the target zone using brachytherapy. The brachytherapy dosage plan including placement position of radioactive source(s) mounted on (a) brachytherapy-catheter(s) and time duration the radioactive source will remain at these position(s). Thus, the brachytherapy dosage plan may include such things as catheter placement and also how long the radioactive source will remain at what position inside the brachytherapy catheter. This embodiment may be advantageous because the same magnetic resonance imaging data is used to plan both the radiotherapy treatment by the external beam radiotherapy system and by a brachytherapy catheter.

The typical workflow is to first perform the irradiating of a target zone using the external beam radiotherapy and then to later treat the same target zone using brachytherapy. A particular difficulty with this is that the external beam radiotherapy system may destroy significant portions of tissue and make it difficult to accurately identify the target zone. In this embodiment the same magnetic resonance image is used to plan both the control of the external beam radiotherapy system and also for the use of a brachytherapy catheter.

The first magnetic resonance data can essentially be used for planning and/or guidance and/or tracking for the external beam radiotherapy system and/or a brachytherapy catheter system. The planning data may also contain data which is descriptive of the applicator or catheter placement.

In another embodiment execution of the instructions further cause the processor to generate external beam radiotherapy system control data for controlling the external beam radiotherapy system to irradiate the subject according to the external beam dosage plan. Essentially in this step the external beam dosage plan is used to generate the commands which are then used to control the external beam radiotherapy system to irradiate the target zone. Execution of the instructions further cause the processor to irradiate the target zone by controlling the external beam radiotherapy system with the external beam radiotherapy system control data. In this step the processor uses the external beam radiotherapy system control data to control the external beam radiotherapy system to irradiate the target zone.

In another embodiment, execution of the instructions further cause the processor to repeatedly acquire monitoring magnetic resonance data from a field of view comprising the target zone. The term 'monitoring magnetic resonance data' is a label for magnetic resonance data that is acquired repeatedly and may be used for the purpose of monitoring the subject. Execution of the instructions further causes the processor to repeatedly reconstruct a monitoring magnetic resonance image from the monitoring magnetic resonance data. Likewise, the term 'monitoring magnetic resonance image' is a label for magnetic resonance image or images which may be used for monitoring the subject. The monitoring magnetic resonance image may be used for a variety of purposes. For instance it may be used for real time control of the external beam radiotherapy system. The monitoring magnetic resonance image or images may also be used for real time control and catheter placement during brachytherapy.

In another embodiment execution of the instructions further cause the processor to repeatedly register the monitoring magnetic resonance image to the external beam dosage plan. This may be useful in the case where the subject has internal or external movement and it may be beneficial to adjust the control of the external beam radiotherapy system. Execution of the instructions further cause the processor to calculate an accumulated dose using the monitoring magnetic resonance image and the external beam radiotherapy system control data. In addition to or alternatively to calculating the accumulated dose an estimated radiobiological effect can also be calculated. The radiological effect could for instance be the equivalent dose or effective dose. In this step knowledge of the external beam radiotherapy system control data is used in combination with the monitoring magnetic resonance image to calculate an accumulated dose for the subject. Furthermore registration of monitoring images retrieved at different points in time, allows to perform longitudinal monitoring of radiation effects and to take this into account additionally. By looking at the monitoring magnetic resonance image it is possible to know where the various portions or pieces of the subject are located at a particular time. It is then known how the radiation from the external beam radiotherapy system travels through the subject using the external beam radiotherapy system control data.

Execution of the instructions further cause the processor to calculate a modification to the external beam dosage plan and/or the brachytherapy dosage plan using the accumulated dosage and the spatially dependent radiation dose. Instead of or in addition to calculating the accumulated dosage, an estimated radiobiological effect can also be calculated. Instead of calculating just the radiation dose the effect on a living tissue may also be considered or calculated. In this step the two dosage plans are modifying knowing what the desired or spatially dependent radiation dose is and what the actual delivered or accumulated dosage is. This may be beneficial because the dose that a subject receives may then be closer or more accurate.

In another embodiment execution of the instructions further cause the processor to display the monitoring magnetic resonance image on a display. This embodiment may be beneficial because it may enable a physician or other medical professional to monitor the subject. For instance this may be useful during the beam therapy and/or during catheter insertion or even after a catheter is inserted into the subject.

In another embodiment the medical instrument further comprises a brachytherapy catheter insertion system for inserting a brachytherapy catheter into the subject.

In another embodiment the medical instrument further comprises a radiation source controller for controlling the insertion and removal of the radiation source into the subject using the brachytherapy catheter (e.g. a so called after loader). Execution of the instructions further causes the processor to acquire the monitoring magnetic resonance data during the insertion of the brachytherapy catheter using the brachytherapy catheter insertion system. In this embodiment the magnetic resonance data is used to monitor the insertion of the brachytherapy catheter using the brachytherapy catheter insertion system. This may be beneficial because it may enable more accurate placing of the brachytherapy catheter. In some examples the brachytherapy catheter and/or the brachytherapy catheter insertion system may contain fiducial marks which simplify or ease the tracking of the inserter or the catheter during the process. As such the monitoring magnetic resonance data may be tailored such that it is able to monitor any fiducial magnetic resonance markers in the inserter or in the catheter. The use of magnetic resonance imaging to guide a catheter in real time is known per se from International Patent Application WO 2012/137148 A1.

In another embodiment the medical instrument further comprises a radiation bunker. A radiation bunker as used herein is a shield to protect an operator or people outside of a treatment area from the harmful effects of ionizing radiation. The radiation bunker is operable for shielding an operator from the radiation source and the beam of ionizing radiation. In this embodiment the radiation bunker is used for shielding two different radiation sources, one is the radiation source from a brachytherapy catheter and also from the radiation generated by the external beam radiotherapy system. This may be beneficial because a single bunker is used for these two separate radiation sources.

In another embodiment the brachytherapy catheter insertion system is robotic. Execution of the instructions further causes the processor to automatically control insertion of the brachytherapy catheter. For instance the brachytherapy dosage plan may contain control commands for the robotic insertion system. This may be beneficial because it may more accurately insert the catheter than a human would.

In another embodiment execution of the instructions further causes the processor to acquire the monitoring magnetic resonance data during placement of the brachytherapy catheter. Execution of the machine-readable instructions further causes the processor to determine a catheter location using the monitoring magnetic resonance data. This for instance may be performed by noticing a lack of signal in a particular region and inferring the location of the catheter or by implementing active tracking coils.

In other embodiments there may be a magnetic resonance imaging fiducial mark on the catheter which enables the easy location of the catheter in space. Execution of the instructions further causes the processor to register the monitoring magnetic resonance image to the first magnetic resonance image. Execution of the instructions further cause the processor to display the catheter location superimposed on the first magnetic resonance image on the display. This embodiment may be particularly beneficial when the target zone is irradiated with the external beam radiotherapy system first. This is because the first magnetic resonance image shows the target zone before any tissues were destroyed by the beam of ionizing radiation. This may greatly enable the ability to place the brachytherapy catheter in the correct location in comparison to when the brachytherapy catheter is guided by a later magnetic resonance image acquired after the target zone has been irradiated with the ionizing radiation. Essentially the monitoring magnetic resonance data is used to locate the catheter and this is then used in conjunction with the first magnetic resonance image to display how the subject's anatomy had looked previously.

In another embodiment the medical instrument comprises the brachytherapy catheter.

In another embodiment execution of the instructions cause the processor to perform irradiation of the target zone using the external beam radiotherapy system and the radiation source controller simultaneously. In this embodiment the beam of ionizing radiation and the brachytherapy radiation source are used simultaneously.

In another embodiment execution of the instructions cause the processor to first perform irradiation of the target zone using the external beam radiotherapy system and to secondly perform irradiation of the target zone using the radiation source controller. This embodiment may be beneficial because the first magnetic resonance image may be used to guide the placement of a catheter using the first magnetic resonance image.

In another embodiment the computer storage further contains a catheter attenuation model descriptive of the attenuation of ionizing radiation by the catheter. Execution of the instructions further cause the processor to calculate an external beam radiation dose plan at least partially using the catheter attenuation model. This example may be beneficial when the catheter is placed before the ionizing radiation beam is used and also for the case when the brachytherapy and the ionizing beam therapy are performed simultaneously. The catheter attenuation model may also include attenuation of the ionizing radiation by a radiation source in the catheter also. Hence, if the catheter is being used to irradiate the patient at the same time as the external beam radiotherapy system or not.

In another aspect the invention provides for a computer program product comprising machine-executable instructions for execution by a processor for controlling the medical instrument. The medical instrument comprises a magnetic resonance imaging system for acquiring magnetic resonance data from the subject within an imaging zone. The medical instrument further comprises an external beam radiotherapy system for irradiating a target zone with a beam of ionizing radiation within the imaging zone. Execution of the instructions causes the processor to acquire first magnetic resonance data from the subject using the magnetic resonance imaging system.

Execution of the instructions further cause the processor to reconstruct a first magnetic resonance image from the first magnetic resonance data. Execution of the instructions further causes the processor to receive planning data. The planning data specifies a spatially dependent radiation dose for the target zone. Execution of the instructions further causes the processor to register the planning data to the first magnetic resonance image. Execution of the instructions further cause the processor to calculate an external beam dosage plan and a brachytherapy dosage plan using the spatially dependent radiation dose and the first magnetic resonance image.

In another aspect the invention may provide for a method of radiation therapy using a medical instrument and a brachytherapy catheter system. The medical instrument comprises a magnetic resonance imaging system for acquiring the magnetic resonance data from a subject within an imaging zone. The medical instrument comprises an external beam radiotherapy system for irradiating the target zone with a beam of ionizing radiation within the imaging zone. The brachytherapy catheter system comprises a brachytherapy catheter. The method comprises acquiring first magnetic resonance data from the subject using the magnetic resonance imaging system. The method further comprises reconstruction a first magnetic resonance image from the first magnetic resonance data. The method further comprises receiving planning data. The planning data specifies at least a spatially dependent radiation dose for the target zone. The method further comprises registering the planning data to the first magnetic resonance image. The method further comprises calculating an external beam dosage plan and a brachytherapy dosage plan using the spatially dependent radiation dose and the first magnetic resonance image.

The method further comprises irradiating the target zone using the external beam radiotherapy system in accordance with the external beam dosage plan. The method further comprises monitoring insertion of the brachytherapy catheter in real time using the magnetic resonance imaging system. The final placement of the brachytherapy catheter is determined using the first magnetic resonance image and the brachytherapy dosage plan. The method further comprises controlling the insertion of the radioactive source into the brachytherapy catheter using the brachytherapy dosage plan. For instance the brachytherapy dosage plan may contain information as to how long the radiation source remains within the brachytherapy catheter.

In another embodiment the brachytherapy catheter is inserted prior to irradiating the target zone.

In another embodiment the brachytherapy catheter is inserted after irradiating the target zone.

In another embodiment the brachytherapy catheter is inserted prior to irradiating the target zone and the target zone is irradiated simultaneously using the external beam radiotherapy system and by insertion of the radiotherapy source into the brachytherapy catheter.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIGS. 2A, 2B, and 2C show a flow chart of a further method;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
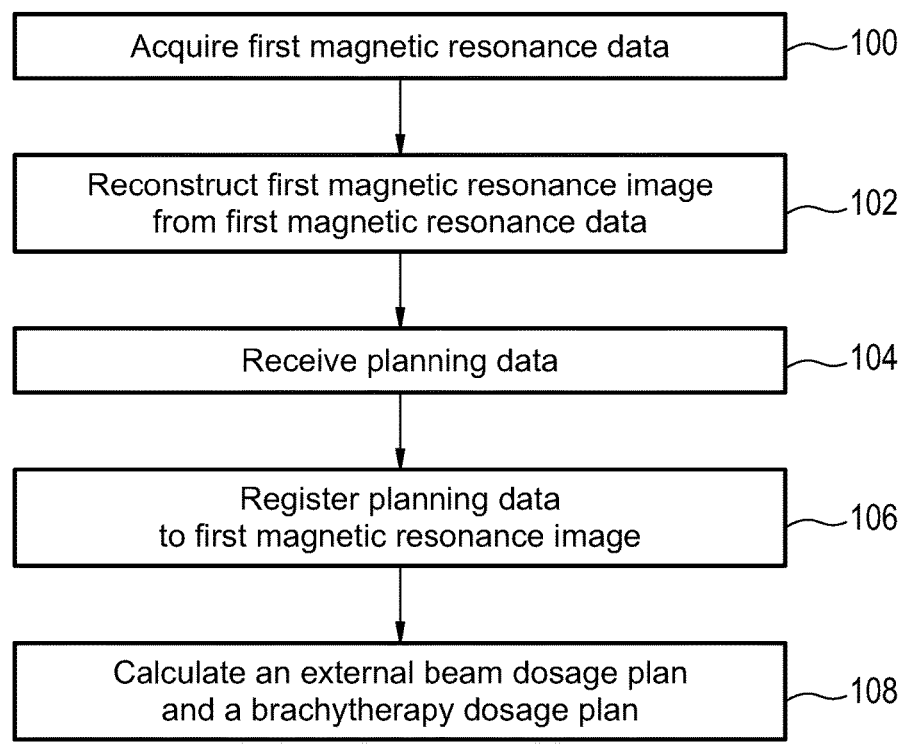
FIG. 1 shows a flowchart of a method.

FIG. 1 shows a flowchart which illustrates an example of a method. The method shown in FIG. 1 can be performed with a magnetic resonance imaging system for acquiring magnetic resonance data from a subject within the imaging zone. The method is also performed with an external beam radiotherapy system for irradiating a target zone with a beam of ionizing radiation within the imaging zone. In step 100 first magnetic resonance data is acquired from the subject using the magnetic resonance imaging system. Next in step 102 a first magnetic resonance image is reconstructed from the first magnetic resonance data. Then in step 104 planning data is received. The planning data specifies a spatially dependent radiation dose for the target zone. Then in step 106 the planning data is registered to the first magnetic resonance image. The planning data may also contain such things as the location of the spatially dependent radiation dose relative to particular anatomical landmarks. This will enable an automated registration of the planning data to the first magnetic resonance image. Then finally in step 108 an external beam dosage plan and a brachytherapy dosage plan is calculated using the spatially dependent radiation dose and the first magnetic resonance image. The first magnetic resonance image may be used for planning both radiation doses and both plans are calculated together at the same time.

Figure 2A:
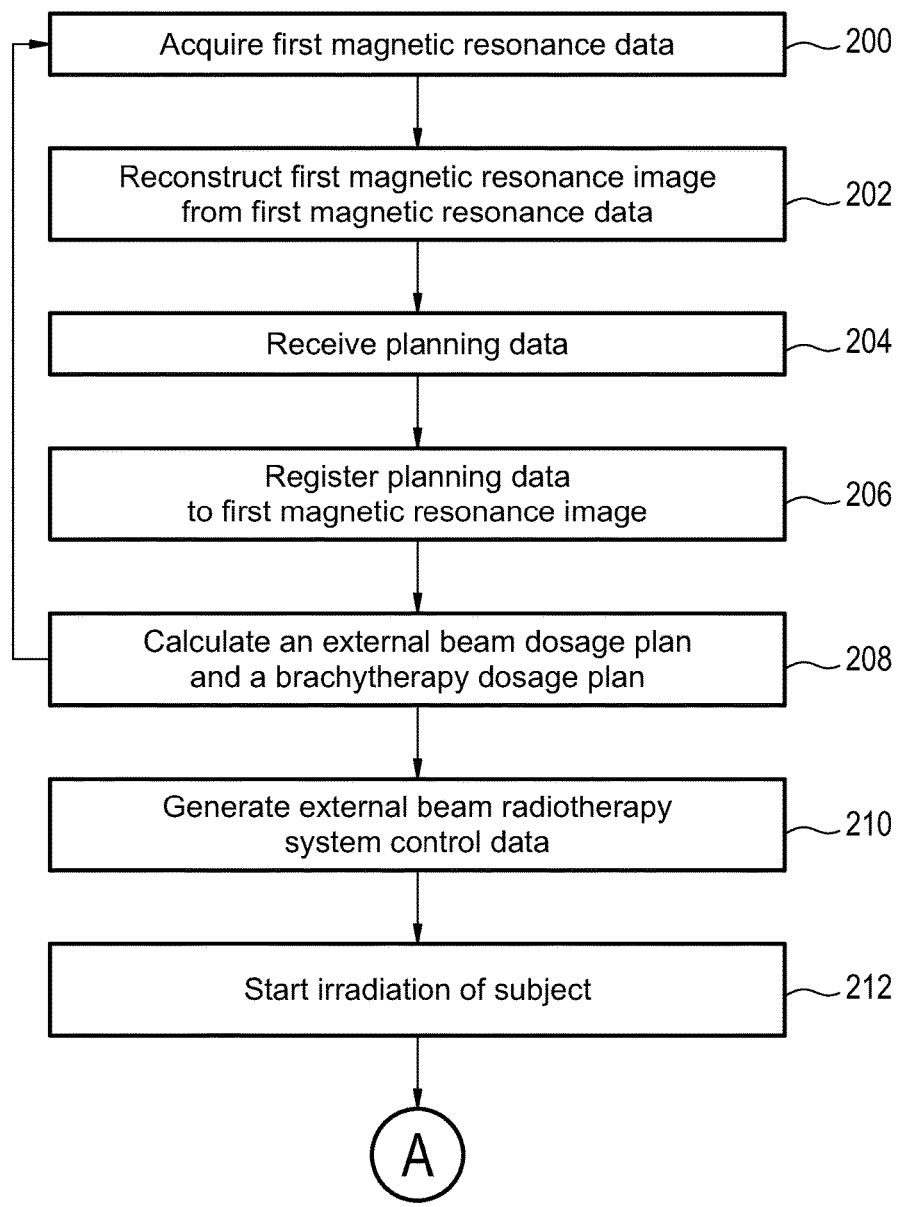

FIG. 2 shows a flowchart which shows a further method. The method shown in FIGS. 2a, 2b and 2c is an expansion of the method shown in FIG. 1. The method is broken across three separate sheets. The circle with an a is used to indicate the transition between FIGS. 2a and 2b and the circle with a b is used to indicate the transition between the Fig. shown in 2b and 2c.

First in step 200 first magnetic resonance data is acquired from the subject using the magnetic resonance imaging data. Next in step 202 a first magnetic resonance image is reconstructed from the magnetic resonance data. Then in step 204 planning data is received. The planning data specifies a spatially dependent radiation dose for the target zone. Next in step 206 the planning data is registered to the first magnetic resonance image. Next in step 208 an external beam dosage plan and a brachytherapy dosage plan is calculated using the spatially dependent radiation dose and the first magnetic resonance image. In step 210 external beam radiotherapy system control data is generated for controlling the external beam radiotherapy system to irradiate the subject according to the external beam dosage plan. The external beam dosage plan may be used to generate specific command sequences or controls which can be used by the processor to control the external beam radiotherapy system to irradiate the target zone.

Then in step 212 the irradiation of the subject is started by controlling the external beam radiotherapy system with the external beam radiotherapy system control data. Next in step 214 monitoring magnetic resonance data is acquired from the field of view comprising the target zone. Next in step 216 a monitoring magnetic resonance image is reconstructed from the monitoring magnetic resonance data. In step 218 the monitoring magnetic resonance data is registered to the external beam dosage plan. In step 220 an accumulated dosage is calculated using the monitoring magnetic resonance image and the external beam radiotherapy system control data. Then in step 222 a modification to the external beam dosage plan and/or the brachytherapy dosage plan is calculated using the spatially dependent radiation dose. If the irradiation of the subject is finished then the method proceeds to step 224 where the irradiation of the subject using the external beam radiotherapy system is halted or stopped. If the irradiation of the subject continues then the method returns back to step 214 and a loop of steps between 214 and 222 are repeated until the irradiation of the target zone is finished.

After the irradiation of the subject 222 is finished, the next step is 226. In step 226 the placement of the brachytherapy catheter is begun. In step 228 the monitoring magnetic resonance data is acquired. In step 230 the monitoring magnetic resonance image is again reconstructed from monitoring magnetic resonance data. Next in step 232 a catheter location is determined using the monitoring magnetic resonance data. This for instance may be used by fiducial markers located within the catheter. Next in step 234 the catheter location is registered to the first magnetic resonance image. In step 236 the catheter location is displayed on the first magnetic resonance image. If the brachytherapy catheter is placed in the correct position, then the method proceeds to step 238 where the placement of the brachytherapy catheter ends. If however the catheter is not correctly placed yet then the method at step 236 goes back to step 228 and these steps are repeated in a loop until the catheter is placed in the correct position. After the end of the placement of the brachytherapy catheter 238 the brachytherapy treatment plan may be executed. This for instance may be done by sending commands to a radiation source controller which is operable for controlling the insertion or removal of a radiation source into the subject using the brachytherapy catheter.

The exact order of the steps shown in FIGS. 2a, 2b and 2c may be organized differently in different examples. For instance the steps 226-238 may in some instances be performed before irradiation of the subject, step 212. When the placement of the catheter 226 happens before the irradiation of the subject 212 it may be possible that the brachytherapy treatment plan is executed 240 during irradiation of the subject, steps 212-224.

Figure 3:
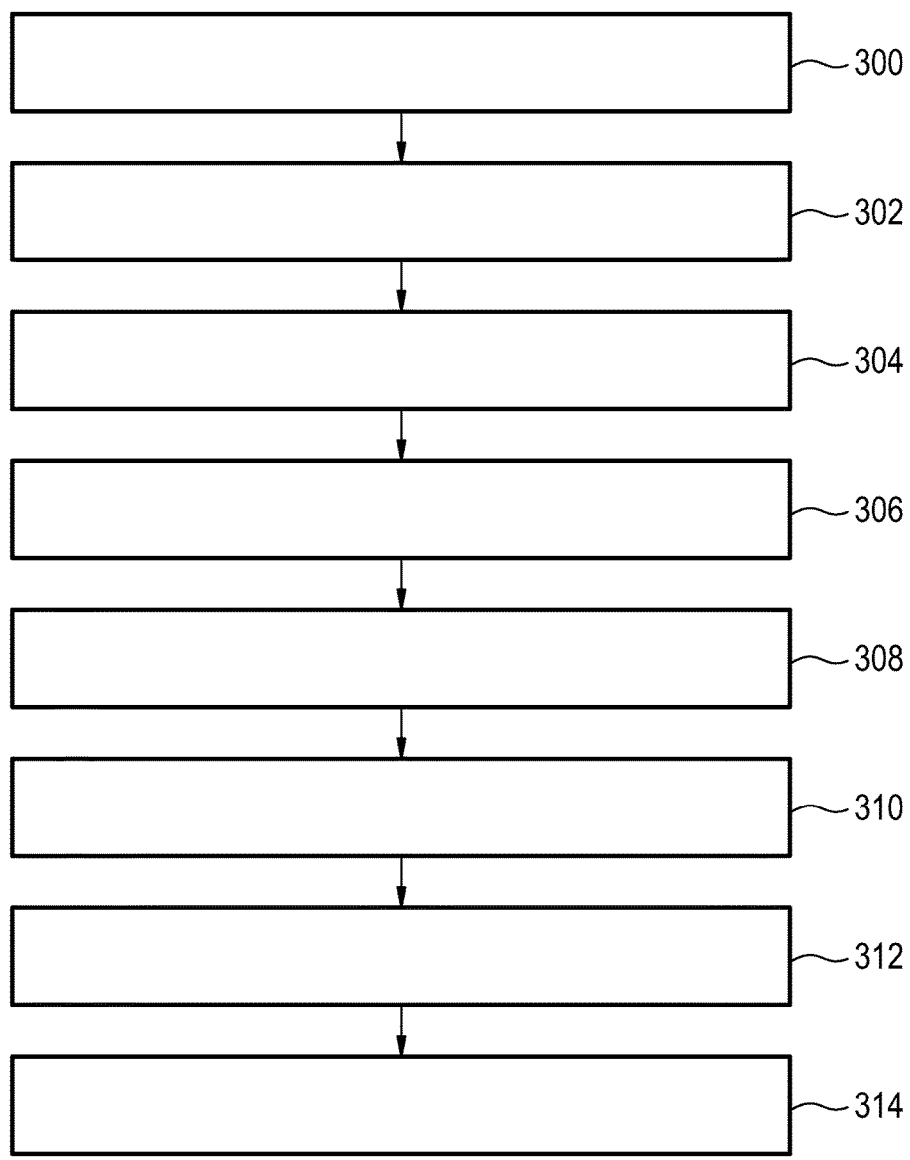
FIG. 3 shows a flowchart of a further method.

FIG. 3 shows a flow diagram which illustrates a further method. The method may be performed using a medical instrument and a brachytherapy catheter system. The medical instrument comprises a magnetic resonance imaging system for acquiring magnetic resonance data from a subject within an imaging zone. The medical instrument further comprises an external beam radiotherapy system for irradiating a target zone with a beam of ionizing radiation within the imaging zone. The brachytherapy catheter system comprises a brachytherapy catheter. First in step 300 first magnetic resonance data is acquired from the subject using the magnetic resonance imaging system. Next in step 302 a first magnetic resonance image is reconstructed from the first magnetic resonance data. Then in step 304 planning data is received. The planning data specifies a spatially dependent radiation dose for the target zone.

Next in step 306 the planning data is registered to the first magnetic resonance image. Then in step 308 an external beam dosage plan and a brachytherapy dosage plan is calculated using the spatially dependent radiation dose and the first magnetic resonance image. Next in step 310 the target zone is irradiated using the external beam radiotherapy system in accordance with the external beam dosage plan. Next in step 312 the insertion of the brachytherapy catheter is inserted and monitored in real time using the magnetic resonance imaging system. The final placement of the brachytherapy catheter is determined using the first magnetic resonance image and the brachytherapy dosage plan. Finally in step 314 the insertion of a radioactive source into the brachytherapy catheter is controlled using the brachytherapy dosage plan. Essentially the brachytherapy dosage plan may contain a duration for which the radioactive source is inserted into the catheter.

Figure 4:
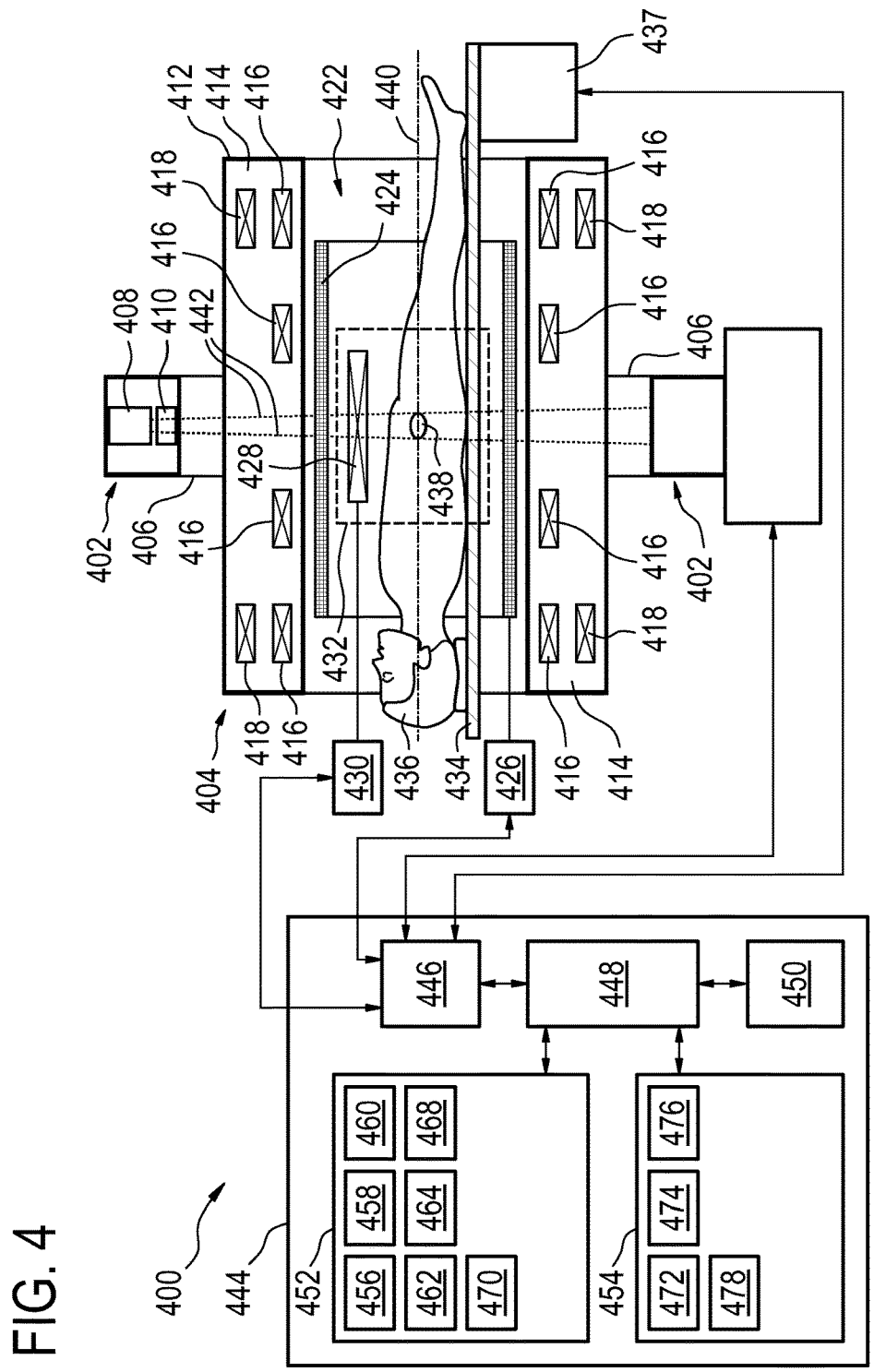
FIG. 4 illustrates an example of a medical instrument.

FIG. 4 shows an embodiment of a medical instrument 400. The medical instrument 400 comprises a external beam radiotherapy system 402 and a magnetic resonance imaging system 404. The external beam radiotherapy system 402 comprises a gantry 406 and a radiotherapy source 408. The gantry 406 is for rotating the radiotherapy source 408 about an axis of gantry rotation 440. Adjacent to the radiotherapy source 408 is a collimator 410. The magnetic resonance imaging system 404 comprises a magnet 412.

It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

The magnet 412 shown in this embodiment is a standard cylindrical superconducting magnet. The magnet 412 has a cryostat 414 with superconducting coils within it 416. There are also superconducting shield coils 418 within the cryostat also. The magnet 412 has a bore 422.

Within the bore of the magnet is a magnetic field gradient coil 424 for acquisition of magnetic resonance data to spatially encode magnetic spins within an imaging zone of the magnet. The magnetic field gradient coil 424 is connected to a magnetic field gradient coil power supply 426.

The magnetic field gradient coil 424 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 426 supplies current to the magnetic field gradient coils. The current supplied to the magnetic field coils is controlled as a function of time and may be ramped or pulsed.

There is a radio frequency coil 428 connected to a transceiver 430. The radio frequency coil 428 is adjacent to an imaging zone 432 of the magnet 412. The imaging zone 432 has a region of high magnetic field and homogeneity which is sufficient for performing magnetic resonance imaging. The radio frequency coil 428 may is for manipulating the orientations of magnetic spins within the imaging zone and for receiving radio transmissions from spins also within the imaging zone. The radio frequency coil 428 may also be referred to as an antenna or channel. The radio frequency coil 428 may contain multiple coil elements. The radio frequency antenna may also be referred to as a channel.

The radio frequency coil 428 and radio frequency transceiver 430 may be replaced by separate transmit and receive coils and a separate transmitter and receiver. It is understood that the radio frequency coil and the radio frequency transceiver are representative. The radio frequency antenna is intended to also represent a dedicated transmit antenna and a dedicated receive antenna. Likewise the transceiver may also represent a separate transmitter and receivers.

Also within the bore of the magnet 422 is a subject support 434 for supporting a subject 436. The subject support 434 may be positioned by a mechanical positioning system 437. Within the subject 436 there is a target zone 438. The axis of gantry rotation 440 is coaxial in this particular embodiment with the cylindrical axis of the magnet 412. The subject support 434 has been positioned such that the target zone 438 lies on the axis 440 of gantry rotation. The radiation source 408 is shown as generating a radiation beam 442 which passes through the collimator 303 and through the target zone 438. As the radiation source 408 is rotated about the axis 440 the target zone 438 will always be targeted by the radiation beam 442. The radiation beam 442 passes through the cryostat 414 of the magnet. The magnetic field gradient coil may have a gap which separate the magnetic field gradient coil into two sections. If present, this gap reduces attenuation of the radiation beam 442 by the magnetic field gradient coil 424. In some embodiments the radio frequency coil 428 may also have gaps or be separated to reduce attenuation of the radiation beam 442.

The transceiver 430, the magnetic field gradient coil power supply 426 and the mechanical positioning system 437 are all shown as being connected to a hardware interface 446 of a computer system 444. The computer system 444 is shown as further comprising a processor 448 for executing machine executable instructions and for controlling the operation and function of the therapeutic apparatus. The hardware interface 446 enables the processor 448 to interact with and control the medical instrument 400. The processor 448 is shown as further being connected to a user interface 450, computer storage 452, and computer memory 454.

The computer storage is shown as containing a collection of pulse sequences 456. A pulse sequence as used herein encompasses a sequence of commands the processor 448 may use to control the magnetic resonance imaging system 404 to acquire magnetic resonance data. The computer storage 452 is shown as further containing first magnetic resonance imaging data 458 which is acquired using the pulse sequence 456. The computer storage 452 is further shown as containing first magnetic resonance image 460 which is reconstructed from the first magnetic resonance image data 458. The computer storage is further shown as containing planning data 462. The planning data 462 for instance could be received via an external network connection, a thumb drive, or even be entered via the user interface 450. The computer storage 452 is further shown as containing a planning data registration 464 which contains the registration between the planning data 462 and the first magnetic resonance image 460. The computer storage 452 is further shown as containing a brachytherapy dosage plan 470 and an external beam dosage plan 468.

The computer memory 454 is shown as containing a control module 472. The control module 472 contains computer-executable code which enables the processor 448 to control the operation and function of the medical instrument 400. The computer memory 454 is shown as further containing an image reconstruction module 474 which enables the processor 448 to reconstruct magnetic resonance data such as the first magnetic resonance imaging data 458 into magnetic resonance images such as the first magnetic resonance image 460. The computer memory 454 is further shown as containing an image registration module 476 which is operable for performing image registration between two images or data descriptive of an image and an image. For example the image registration module 476 contains computer-executable code which enables the processor 448 to register the planning data 462 to the first magnetic resonance image 460. The computer memory 454 is further shown as containing a radiotherapy planning module 478 which was used to generate the external beam dosage plan 468 and the brachytherapy dosage plan 470 using the spatially dependent radiation dose within the planning data 462 and the first magnetic resonance image 460. It is of course implicit that the registration 464 is also used by the radiotherapy planning module 478.

The computer memory 454 may contain additional software modules. For instance it may contain a software module to generate commands for controlling the external beam radiotherapy system using the external beam dosage plan. The memory may also contain a software module for modifying the external beam dosage plan, brachytherapy dosage plan, and/or the commands for controlling the externally beam radiotherapy system using monitoring magnetic resonance data.

Figure 5:
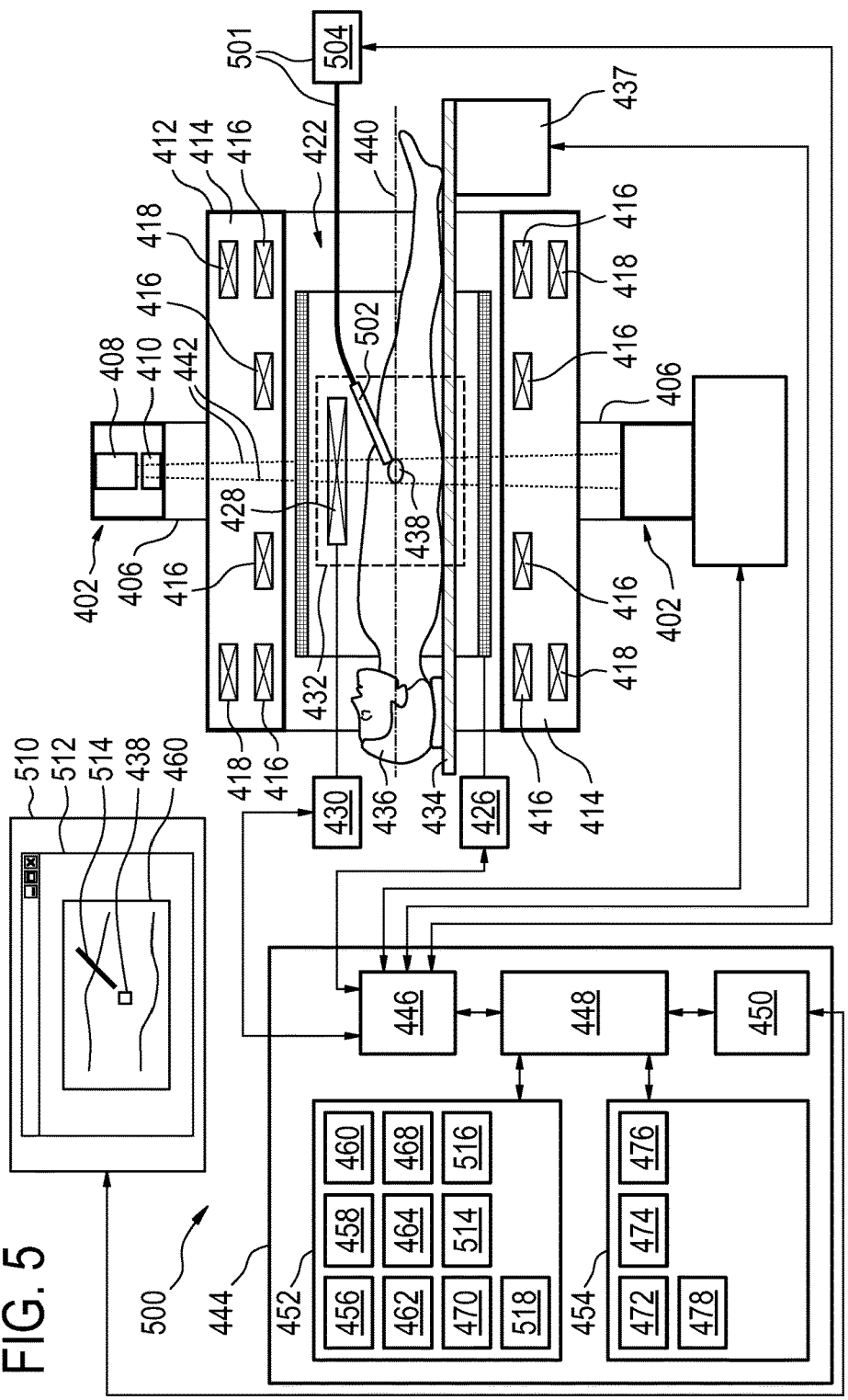
FIG. 5 illustrates a further example of a medical instrument.

FIG. 5 shows a further example of a medical instrument 500. The medical instrument shown in FIG. 5 is similar to the medical instrument shown in FIG. 4. There are however several additional components and functionalities. The medical instrument comprises a brachytherapy catheter insertion system 501. The brachytherapy catheter insertion system 501 comprises a brachytherapy catheter 502 and a radiation source controller 504 which is operable for inserting and retracting a radioactive source into the brachytherapy catheter 502. The brachytherapy catheter 502 is shown as being inserted into the subject 434 and in close proximity to the target zone 438. The display 510 is shown as being connected to the user interface 450. On the display 512 a graphical user interface 512 is shown. The graphical user interface 512 is displaying the first magnetic resonance image 460. On the first magnetic resonance image 460 the location of the target zone 438 is shown and also a position 514 of the catheter 502.

The computer storage 452 is shown as further containing a brachytherapy catheter location 514 that is superimposed on the magnetic resonance image 460. The computer storage is further shown as containing monitoring magnetic resonance data 516 that was acquired using the pulse sequence 456. The computer storage 452 is also shown as containing the monitoring magnetic resonance image 518 that was reconstructed using the image reconstruction module 474 and the monitoring magnetic resonance data 516. The computer memory 454 is further shown as containing a catheter location module 520. The catheter locator module 520 is operable for detecting the location of the brachytherapy catheter 502 within the monitoring magnetic resonance image 518 and deriving a brachytherapy catheter location 514.

FIG. 5 illustrates how the location of the catheter 514 can be derived from later monitoring magnetic resonance images 518 while the position is still superimposed on the first magnetic resonance image 460.

Figure 6:
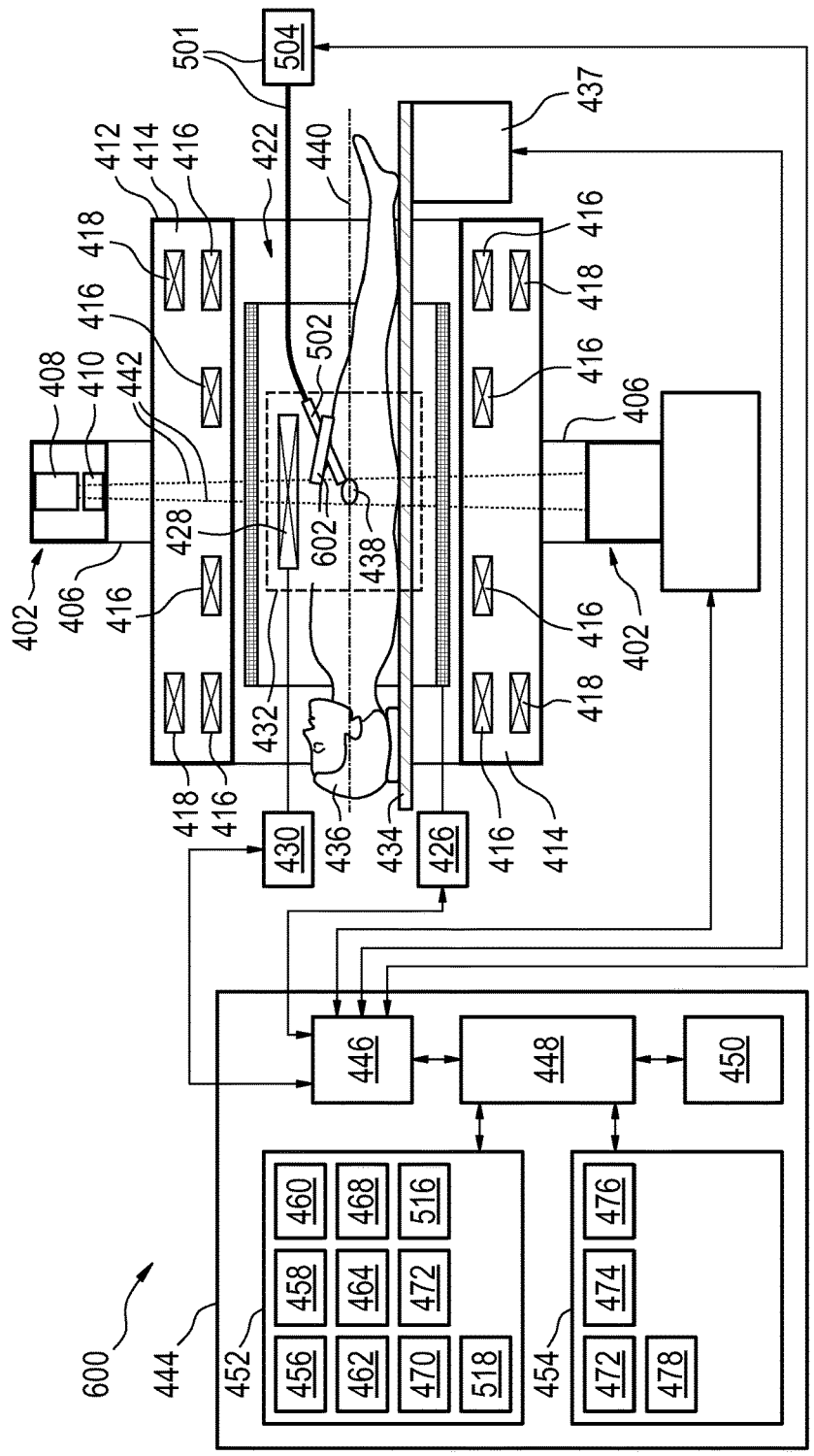
FIG. 6 illustrates a further example of a medical instrument.

FIG. 6 shows a further example of a medical instrument 600. The medical instrument 600 is similar to that shown in FIGS. 5 and 4. However, in this example there is an inserter 602 positioned on the surface of the subject 436. The inserter 602 may be used as an aid to help position the catheter 502 properly as it is inserted into the subject 436. The inserter 602 may also be positioned with the aid of the magnetic resonance imaging system 412. For instance fiducial markers such as those incorporated into the catheter 502 may also be incorporated into the inserter 602.

Figure 7:
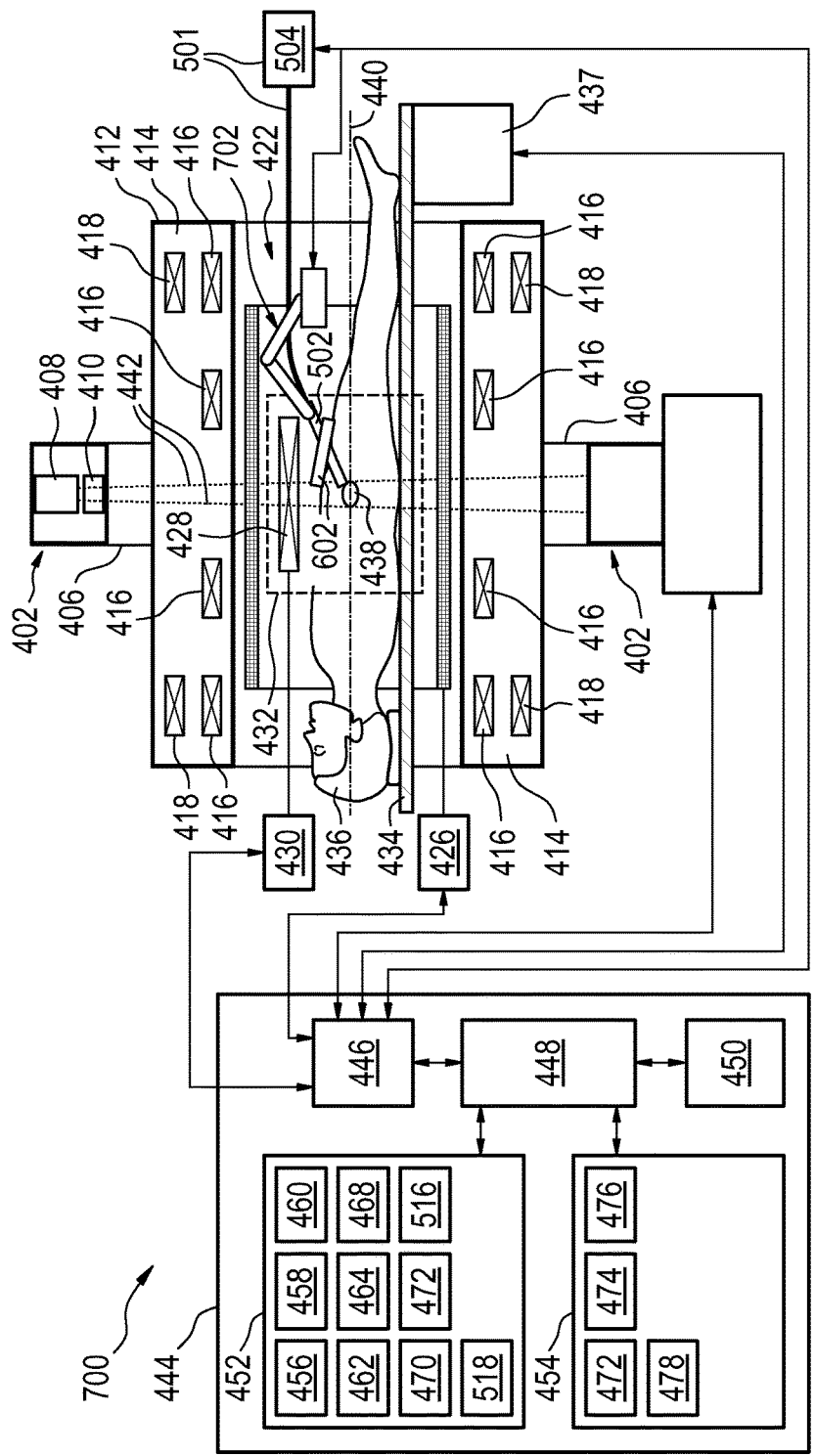
FIG. 7 illustrates a further example of a medical instrument.

FIG. 7 shows an example of a medical instrument 700. The medical instrument 700 is similar to that shown in FIGS. 4-6.

In comparison with the medical instrument 600 shown in FIG. 7 the medical instrument 700 additionally comprises a catheter insertion system 702 for automatically inserting the catheter 502 using the catheter inserter 602. This enables the processor 448 to automatically insert the catheter 502 into the subject 436. According to the brachytherapy dosage plan 470, the brachytherapy dosage plan 470 may contain information on the catheter placement and also information on how long a radiation source should be inserted into the catheter 502.

The integration of an MR and a Linear Accelerator (LINAC) system allows real-time monitoring of the patient during the external beam radiotherapy (EBRT) treatment session. Focal boost therapy regimes employ additional—separate from EBRT—brachytherapy sessions to amplify the treatment effect locally. Precise localization of the brachytherapy catheters (e.g. via CT, MR, US) is an essential prerequisite for a correct applicator placement and focal therapy.

The proposed solution may allow integration of the workflow of these two (EBRT+brachy), currently separate, parts of the therapy seamlessly. This leads to higher patient acceptance (no extra turn-in for brachytherapy), integrated dose planning (EBRT+brachy) and real-time monitoring of catheter placement/treatment.

Optionally an extension of the few brachy-EBRT sessions would allow to treat the patient in the linac bunker, eliminating the need for additional (HDR) brachytherapy bunker.

Integration of an MR and a Linac system allows real-time monitoring of the patient during the external beam radiotherapy (EBRT) treatment sessions. The usual treatment course is 5 EBRT fractions/sessions per week over 6 weeks. Each session taking about 15 minutes. Patients do usually come to the hospital for every separate treatment session.

Focal therapies, such as high dose rate brachytherapy (HDR), on the other hand take only a few sessions over up to a couple of hours (e.g. PDR). But patients do usually stay at the hospital for the prescribed therapy duration (around 1 or 2 days). Recent studies performing a very much shortened therapy course (e.g. only one HDR dose application—hypofractionation) show promising results. Precise localization of the brachytherapy catheters (e.g. via CT, MR, US) is an essential prerequisite for a correct applicator placement and for such novel focal therapy single session treatments.

In selected cases focal boost therapy is combined with EBRT, where the brachytherapy sessions amplify the treatment effect locally. This is usually done after the EBRT treatment course is finished.

Problems or disadvantages overcome by examples:

Sequential performance of EBRT and brachytherapy has several disadvantages:
- patient acceptance of additional effort for local therapy (hospital visit, planning and treatment sessions) is relatively low,
- Tumor/tissue changes towards the end of the EBRT course complicate lesion identification for focal therapy,
- Repeated structure delineation effort and detached planning systems for EBRT and brachy,
- rising use/acceptance of MR for focal therapy planning/guidance with very limited access to devices,
- additional cost of brachytherapy bunker for treatment sessions.

All of these problems are solved/reduced by the proposed workflow integration.

The proposed method includes a workflow and software tools which allow the use of the MR-Linac system and bunker for focal therapies and the mutual data exchange of the two planning systems.

DETAILED DESCRIPTION OF HOW TO BUILD AND USE EXAMPLES

For the proposed integration of the EBRT and focal therapy workflow several levels are possible, but some elements include:
- extension of selected EBRT sessions for focal therapy application,
- use of functional/anatomic imaging data from MR-Linac sessions for focal therapy planning,
- use of EBRT planning data (e.g. updated delineated structures and dose prescription) as direct input for focal therapy planning and cumulative dose for EBRT+brachy irradiation
- MR guided insertion of focal therapy applicators (catheters) inside MR-Linac (with switched off Linac),
- focal treatment inside Linac bunker.

Some more advanced regimes could include the focal treatment during EBRT which would include an absorption correction for the brachytherapy applicator and source. Insertion of the applicators (catheters) could possibly be done robot assisted.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 400 medical instrument
402 external beam radiotherpay system
404 magnetic resonance imaging system
406 gantry
408 radiotherapy source
410 collimator
412 magnet
414 cryostat
416 superconducting coil
418 superconducting shield coil
422 bore
424 magnetic field gradient coil
426 magnetic field gradient coil power supply
428 radio frequency coil
430 transciever
432 imaging zone
434 subject support
436 subject
437 mechanical positioning system
438 target zone
440 axis of gantry rotation
442 radiation beam
444 computer system
446 hardware interface
448 processor
450 user interface
452 computer storage
454 computer memory
456 pulse sequences
458 first magentic resonance imaging data
460 first magnetic resonance image
462 planning data
464 planning data registration
468 external beam dosage plan
470 brachytherapy dosage plan
472 control module
474 image reconstruction module
476 image registration module
478 radiotherapy planning module
500 medical instrument
501 brachytherapy catheter insertion system
502 brachytherapy catheter
504 radiation source controller
510 display
512 user interface
514 brachatherapy catheter location
516 monitoring magnetic resonance data
518 monitoring magnetic resonance image
520 catheter locator module
600 medical instrument
602 catheter inserter
700 medical instrument
702 robotic insertion system

The invention claimed is:

1. A medical instrument comprising:
a magnetic resonance imaging system for acquiring magnetic resonance data from a subject within an imaging zone;
an external beam radiotherapy system for irradiating a target zone with a beam of ionizing radiation within the imaging zone;
a memory for storing machine executable instructions;
a processor for controlling the medical instrument, wherein execution of the instructions cause the processor to:
acquire magnetic resonance data from the subject using the magnetic resonance imaging system;
reconstruct a magnetic resonance image from the magnetic resonance data;
receive planning data, wherein the planning data specifies a spatially dependent radiation dose for the target zone;
register the planning data to the magnetic resonance image; and
calculate an external beam dosage plan and a brachytherapy dosage plan using the spatially dependent radiation dose and the magnetic resonance image wherein the same magnetic resonance image is used to calculate both the external beam dosage plan and the brachytherapy dosage plan and where
the external beam dosage plan is a plan or commands for irradiating the target zone using the external beam radiotherapy system, and
the brachytherapy dosage plan is a plan for irradiating the target zone using brachytherapy, the brachytherapy dosage plan including placement position of radioactive source(s) mounted on (a) brachytherapy-catheter(s) and time duration the radioactive source will remain at these position(s).

2. The medical instrument of claim 1, wherein execution of the instructions further cause the processor to:
generate external beam radiotherapy system control data for controlling the external beam radiotherapy system to irradiate the subject according to the external beam dosage plan; and
irradiate the target zone by controlling the external beam radiotherapy system with the external beam radiotherapy system control data.

3. The medical instrument of claim 1, wherein execution of the instructions further causes the processor to repeatedly:
acquire monitoring magnetic resonance data from a field of view comprising the target zone; and
reconstruct a monitoring magnetic resonance image from the monitoring magnetic resonance data.

4. The medical instrument of claim 3, wherein execution of the instructions further cause the processor to repeatedly:
register the monitoring magnetic resonance image to the external beam dosage plan;
calculate an accumulated dosage and/or radiobiological effect using the monitoring magnetic resonance image and the external beam radiotherapy system control data;
calculate a modification to the external beam dosage plan and/or the brachytherapy dosage plan using the accumulated dosage and/or the radiobiological effect and the spatially dependent radiation dose.

5. The medical instrument of claim 3, wherein execution of the instructions further causes the processor to repeatedly display the monitoring magnetic resonance image on a display.

6. The medical instrument of claim 5, wherein the medical instrument further comprises a brachytherapy catheter insertion system for inserting a brachytherapy catheter into the subject, wherein the medical instrument further comprises a radiation source controller for controlling the insertion and removal of a radiation source into the subject using the brachytherapy catheter, wherein execution of the instructions further cause the processor to acquire the monitoring magnetic resonance data during insertion of the brachytherapy catheter using the brachytherapy catheter insertion system.

7. The medical instrument of claim 6, wherein the brachytherapy catheter insertion system is robotic, wherein execution of the instructions further causes the processor to automatically control insertion of the brachytherapy catheter.

8. The medical instrument of claim 6, wherein execution of the instructions further causes the processor to:
acquire the monitoring magnetic resonance data during placement of the brachytherapy catheter,
determine a catheter location using the monitoring magnetic resonance data,
register the monitoring magnetic resonance image to the magnetic resonance image, and
display the catheter location superimposed on the magnetic resonance image on the display.

9. The medical instrument of claim 6, wherein the medical instrument comprises the brachytherapy catheter.

10. The medical instrument of claim 6, wherein execution of the instructions causes the processor to one of:
perform irradiation of the target zone using the external beam radiotherapy system and the radiation source controller simultaneously, or
first perform irradiation of the target zone using the external beam radiotherapy system and second perform irradiation of the target zone using the radiation source controller.

11. The medical instrument of claim 6, wherein the memory further contains a catheter attenuation model descriptive of the attenuation of ionizing radiation by the catheter, and wherein execution of the instructions causes the processor to calculate the external beam dosage plan at least partially using the catheter attenuation model.

12. A computer readable storage medium storing machine executable instructions for execution by a processor for controlling a medical instrument, wherein the medical instrument comprises a magnetic resonance imaging system for acquiring magnetic resonance data from a subject within an imaging zone, wherein the medical instrument further comprises an external beam radiotherapy system for irradiating a target zone with a beam of ionizing radiation within the imaging zone, wherein execution of the instructions cause the processor to:
acquire magnetic resonance data from the subject using the magnetic resonance imaging system;
reconstruct a magnetic resonance image from the magnetic resonance data;
receive planning data, wherein the planning data specifies a spatially dependent radiation dose for the target zone;
register the planning data to the magnetic resonance image; and
calculate an external beam dosage plan and a brachytherapy dosage plan using the spatially dependent radiation dose and the magnetic resonance image and where the external beam dosage plan is a plan or commands for irradiating the target zone using the external beam radiotherapy system and
the brachytherapy dosage plan is a plan for irradiating the target zone using brachytherapy, the brachytherapy dosage plan including placement position of radioactive source(s) mounted on one or more catheters and time duration the radioactive source will remain at these position(s) and
the computer readable medium further stores a catheter attenuation model descriptive of the attenuation of ionizing radiation by the one or more catheters, and wherein execution of the instructions causes the processor to calculate the external beam dosage plan at least partially using the catheter attenuation model.

13. A method of radiation therapy using a medical instrument and a brachytherapy catheter system, wherein the medical instrument comprises a magnetic resonance imaging system for acquiring magnetic resonance data from a subject within an imaging zone, wherein the medical instrument comprises an external beam radiotherapy system for irradiating a target zone with a beam of ionizing radiation within the imaging zone, wherein the brachytherapy catheter system comprises a brachytherapy catheter, wherein the method comprises:
acquiring magnetic resonance data from the subject using the magnetic resonance imaging system;
reconstructing a magnetic resonance image from the magnetic resonance data;
receiving planning data, wherein the planning data specifies a spatially dependent radiation dose for the target zone;
registering the planning data to the magnetic resonance image;
calculating an external beam dosage plan and a brachytherapy dosage plan using the spatially dependent radiation dose and the magnetic resonance image;
irradiating the target zone using the external beam radiotherapy system in accordance with the external beam dosage plan;
monitoring insertion of the brachytherapy catheter in real time using the magnetic resonance imaging system, wherein a final placement of the brachytherapy catheter is determined using the magnetic resonance image and the brachytherapy dosage plan;
controlling the insertion of a radioactive source into the brachytherapy catheter using the brachytherapy dosage plan and where
the external beam dosage plan is a plan or commands for irradiating the target zone using the external beam radiotherapy system and
the brachytherapy dosage plan is a plan for irradiating the target zone using brachytherapy, the brachytherapy dosage plan including placement position of radioactive source(s) mounted on (a) brachytherapy-catheter(s) and time duration the radioactive source will remain at these position(s) and
the brachytherapy catheter is inserted prior to irradiating the target zone.

14. The method of claim 13, wherein the target zone is irradiated simultaneously using the external beam radiotherapy system and by insertion of the radioactive source into the brachytherapy catheter.

* * * * *